United States Patent [19]
Haley

[11] Patent Number: 5,422,640
[45] Date of Patent: Jun. 6, 1995

[54] BREATH ACTUATED POINTER TO ENABLE DISABLED PERSONS TO OPERATE COMPUTERS

[75] Inventor: Vincent L. Haley, Raleigh, N.C.

[73] Assignee: North Carolina State University, Raleigh, N.C.

[21] Appl. No.: 844,141

[22] Filed: Mar. 2, 1992

[51] Int. Cl.$^6$ ............................ H03K 17/94; B41J 5/00
[52] U.S. Cl. ................................. 341/21; 340/825.19; 400/87
[58] Field of Search ............................ 340/825.19, 407; 341/20, 21; 379/52; 128/774, 776, 777; 74/471 XY; 434/112–117; 200/DIG. 2; 400/87; 128/719; 361/170, 178

[56] References Cited

U.S. PATENT DOCUMENTS

| | | | |
|---|---|---|---|
| 3,795,281 | 3/1974 | Cloran | 173/30 |
| 4,486,630 | 12/1984 | Fetchko | 200/52 R |
| 4,562,432 | 12/1985 | Sremac | 340/825.19 X |
| 4,828,418 | 5/1989 | Sauer et al. | 401/6 |
| 4,993,308 | 2/1991 | Villeneuve | 340/825.19 X |

OTHER PUBLICATIONS

IBM Technical Disclosure Bulletin vol. 32 No. 9B Feb. 1990, (all pages).
IBM Technical Disclosure Bulletin vol. 33 No. 12 May 1991 (all pages).

*Primary Examiner*—Brent A. Swarthout
*Assistant Examiner*—Thomas J. Mullen, Jr.
*Attorney, Agent, or Firm*—Richard E. Jenkins

[57] ABSTRACT

This invention relates to a device to allow a handicapped person with limited or no use of the hands to use a personal computer. The device includes a base which includes an inclined support onto which a computer keyboard is positioned. A support arm extends generally upwardly therefrom and is articulated for inward and vertical pivotable movement. A pointer is mounted on the support arm which is adapted to be articulated horizontally so as to position the nose end thereof adjacent a computer key to be depressed. The pointer is manipulated by the face of the operator who turns his head in the direction in which he desires the pointer to horizontally move, and the pointer is actuated outwardly by imparting a breath into a breath port of the pointer. The breath is detected by a pressure sensor transducer which actuates a solenoid in order to extend the nose thereof to depress a desired computer keyboard key.

18 Claims, 12 Drawing Sheets

BREATH ACTUATED POINTER TO ENABLE DISABLED PERSONS TO OPERATE COMPUTERS

TECHNICAL FIELD

The present invention relates to a device to permit a person with limited or no use of the hands to operate the keyboard of a computer or a similar type of office equipment.

RELATED ART

The device of the present invention is designed to provide disabled individuals who have full use of their head and neck with the ability to utilize and use personal computers. In the United States there are a large number of individuals over the age of 65 who are not easily able to execute everyday tasks. Also, there are over 38,000,000 individuals who can be classified as physically or mentally challenged by the demands of their daily lives. Together, these two groups represent a very large number of individuals, perhaps as much as ⅓ of the total population of the United States, who have special needs for living. The special needs exist for these citizens both in the home and in the workplace. The workplace of today where the primary tool is the computer is where these individuals are especially disadvantaged in their ability to satisfactorily perform. In view of the fact that the personal computer has proliferated both in the workplace as well as in the home environment, there is a very great need for a device which would enable the elderly and/or handicapped to be able to access and utilize personal computers. Towards this end, applicant has invented a device which enables quadriplegics and others who only have the use their head, neck and shoulders to efficiently input information and utilize a personal computer.

There is also a recognized need today for a device such as that developed by applicant in view of the 1989 "Americans With Disabilities Act" which requires employers to make reasonable accommodations to the limitations of a qualified disabled person. Although applicant's invention cannot meet the specific needs of all disabled people, the novel device will enable citizens who have spinal cord injuries but who have retained head and neck movement to utilize existing personal computer keyboards and thereby eliminate the need for prospective employers to purchase additional equipment or make costly equipment modifications for these disabled individuals.

U.S. Pat. No. 4,828,418 to Sauer et al. discloses a representative prior art effort to develop a device to enable quadriplegic individuals with only limited or no use of the hands to perform certain tasks such as operating the keyboard of a personal computer. However, as is well known to those familiar with the art, this type of mouth held device suffers severe shortcomings since it must be placed into and retained in the mouth during use. This can prevent speech as well as cause undesirable salivation within the mouth. Similar devices are known which attach to the head of the individual, but these devices also suffer numerous shortcomings including precluding the individual using the device from turning their head and engaging in conversation without disrupting the work being performed on the personal computer keyboard.

Both of the aforementioned devices also have been found to be undesirable since they add to the stigma of the disabled person in view of the fact that they are either placed in the mouth or are strapped to the head of the user. This prevents the user from disassociating himself from the device when it is not being used to manipulate the keyboard of a personal computer and clearly identifies the individual as being disabled by its presence in their mouth or its securement to their head. By contrast, applicant's novel device does not require any mouth contact and is not in any fashion secured to the head. Thus, the disabled individual can utilize the device as desired to manipulate a personal computer keyboard and then withdraw therefrom for normal conversation and social interaction with others.

DISCLOSURE OF THE INVENTION

In accordance with the present invention, applicant provides an improved device for permitting a person with limited or no use of the hands to operate the keyboard of a computer or a similar type of office equipment. The device comprises a base including means for supporting a computer keyboard or a similar type of office equipment in a generally upright position. A support arm is secured at one end to the base and extends generally outwardly therefrom, and an elongate pointer element is adjustably mounted at the other end of the support arm to be used for operative engagement of a personal computer keyboard positioned on the base. The elongate pointer element has a proximal end adapted to be engaged by the face of the operator and a distal end adapted to be selectively actuated by the operator to move from a first retracted position to a second extended position and back to the retracted position. The elongate pointer element is also provided with hands-free operator actuator means to allow the operator to position the distal end of the pointer adjacent a desired key of the personal computer keyboard and to then depress the designated key.

It is therefore the object of this invention to provide a device to enable disabled individuals with limited or no use of the hands to operate the keyboard of a personal computer or a similar type of office equipment.

It is another object of the present invention to provide a quadriplegic person with the ability to utilize a personal computer in the home or office environment.

It is yet another object of the present invention to provide a device which enables a quadriplegic person to utilize a personal computer in the home or workplace environment without requiring modification to the personal computer.

It is still another object of the present invention to provide a device which can be utilized by quadriplegics and similarly disabled persons having little or no use of the hands to operate a personal computer in an efficient and effortless manner which has not heretofore been possible.

Some of the objects of the invention having been stated, other objects will become evident as the description proceeds, when taken in connection with the following drawings.

BEST MODE FOR CARRYING OUT THE INVENTION

Figure 1:
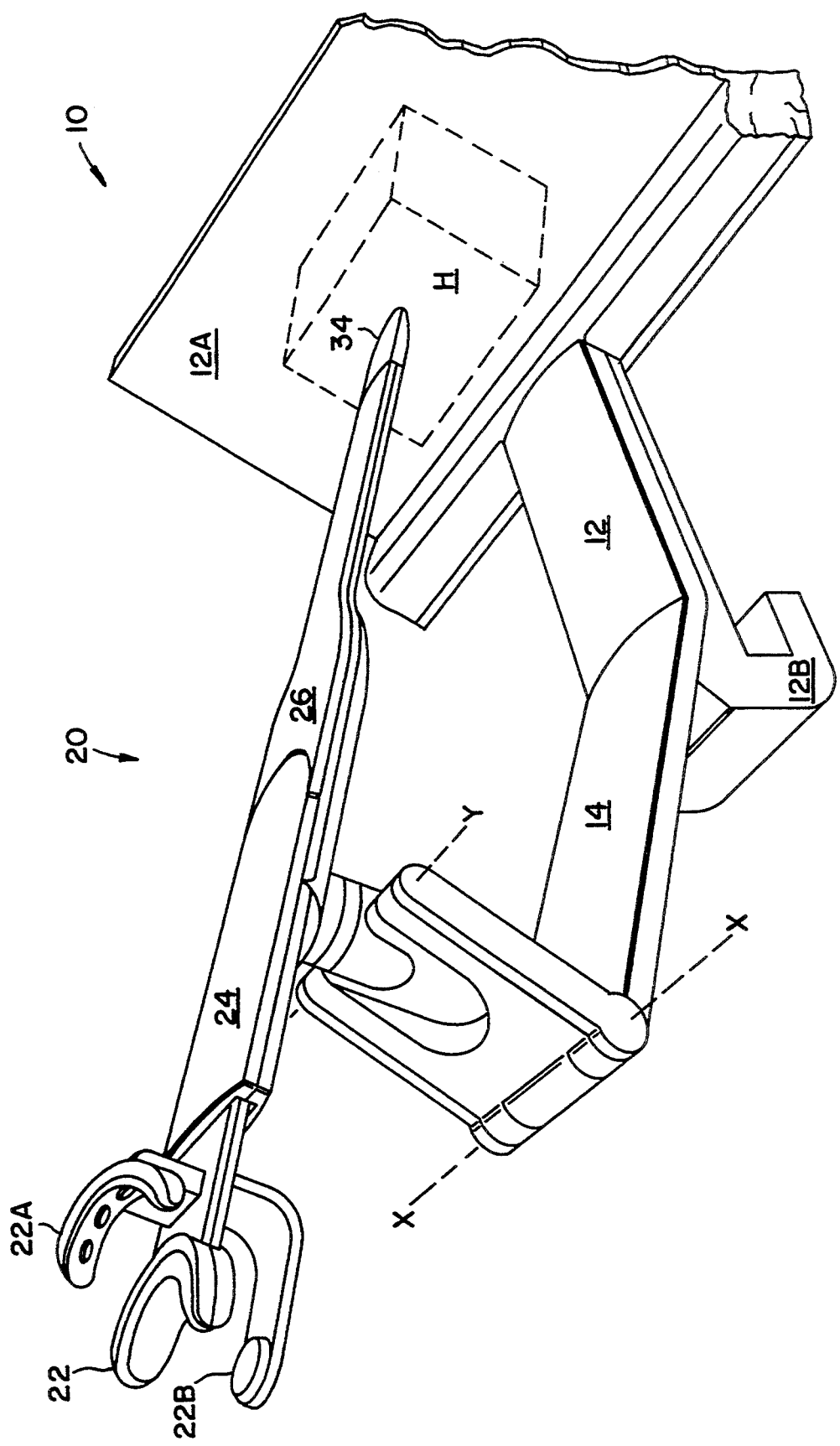
FIG. 1 is a perspective view of one embodiment of the device of the present invention.

Referring now to the drawings, a preferred embodiment of the device 10 is shown which permits a person with limited or no use of the hands to operate a computer keyboard or similar type of office or home equipment. Device 10 is particularly well suited to enable individuals who have spinal cord injuries and have retained only head and neck movement to access and use existing and unmodified computer keyboards so as to eliminate the need for perspective employers to purchase additional equipment or make costly equipment modifications. Device 10 was developed as a significant improvement over previously known "head sticks" and "mouth sticks" utilized by quadriplegic individuals which are either strapped to the head or placed in the mouth, respectively. In addition to the obvious disadvantages of such previously known devices utilized to operate a computer keyboard and the like, the "head sticks" and "mouth sticks" add to the stigma of the disabled person whereas device 10 allows the user to withdraw therefrom at any time during manipulation of a computer keyboard therewith to engage in conversation.

Device 10 includes a base 12 having an upright inclined support 12A for supporting the keyboard C of a computer thereon at a preferred angle of about 60° relative to the horizontal work surface upon which base 12 rests. Shown on keyboard C are representative keys K1, K2, K3 and K4. Base 12 also has a leading edge 12B designed to suitably engage the edge of an office desk or similar work surface at which the operator of device 10 will be inputting information into a computer keyboard C.

Figure 5:
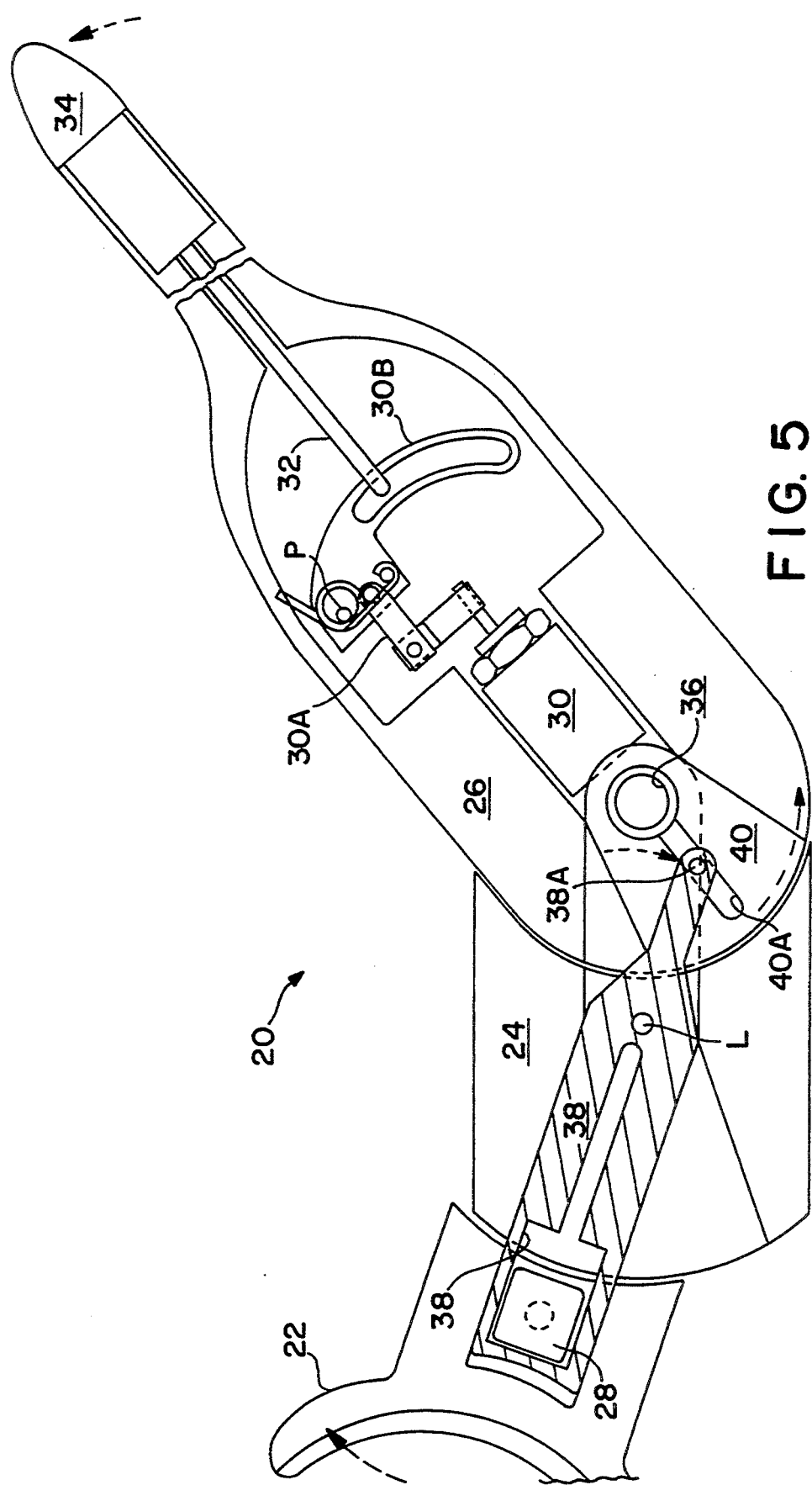
FIG. 5 is a horizontal sectional view of the pointer element of the device of the present invention wherein the pointer element has been articulated.
Figure 6:
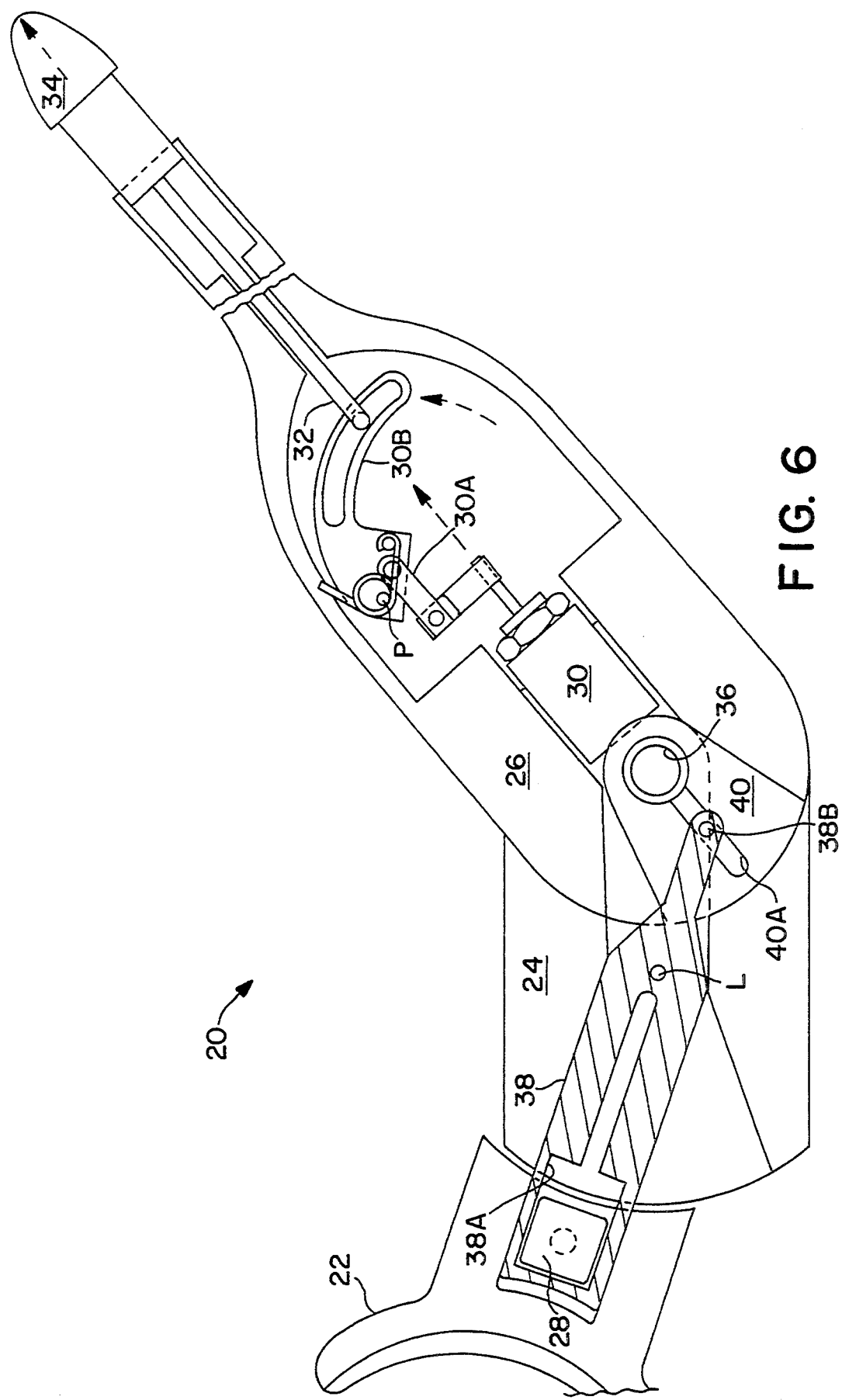
FIG. 6 is a horizontal sectional view of the pointer element of the device of the present invention wherein the pointer element has been articulated and the distal end extended.
Figure 7:
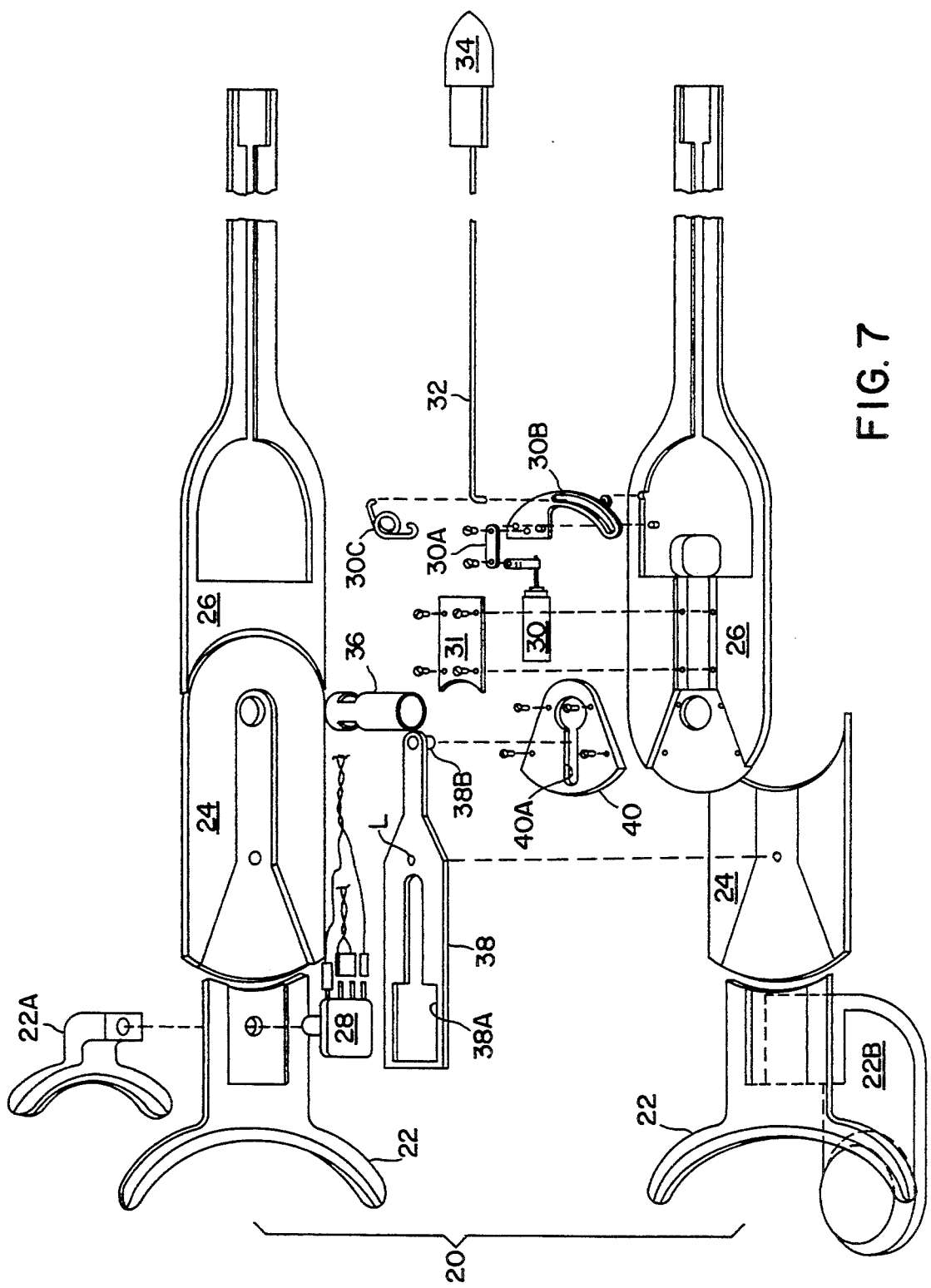
FIG. 7 is an exploded view of the device of the pointer element of the present invention.

An articulated support arm 14 extends outwardly and upwardly from base 12 and the top portion (see FIG. 1) can be pivotably moved relative to the bottom portion about horizontal axis X. A hands-free breath actuated pointer, generally designated 20, is pivotably mounted to the top end of support arm 14 so as to be pivotable about horizontal axis Y (see FIG. 1). Pointer 20, as best seen in FIGS. 4–7, comprises two relatively horizontally pivotably movable sections, proximal section 22 and distal section 24. As best seen in FIG. 7, chin engagement 22, proximal section 24 and distal section 26 are formed from upper and lower housing sections which when mated together serve to contain the electromechanical components of pointer 20.

As can be seen with reference to FIG. 7, pointer 20 further includes breath port 22A mounted to the top housing of chin engagement 22 and chin rest 22B mounted to the bottom housing thereof. Breath port 22A fluidly communicates with pressure transducer 28 which serves to detect air breaths which are blown into breath port 22A by the operator of pointer 20. Although many different types of pressure sensors or transducers may be utilized, applicant presently contemplates that a preferred pressure transducer 28 is available from the Microswitch Division of Honeywell Corporation as Catalog Element No. 170PC.

Pressure sensor or transducer 28 is electrically connected through suitable circuitry such as the representative circuit in FIGS. 8A–8E which serves to detect the low level electrical signal of transducer 28 and convert it to a high current pulse which is then applied to solenoid 30 positioned beneath solenoid retainer plate 31 in the lower housing of distal section 26. Solenoid 30 translates its "push" motion through solenoid cam link 30A and nose extender cam 30B in order to force link rod 32 and nose 34 at the end thereof outwardly in order to strike a key of computer keyboard C. Spring 30C serves to urge extender cam 30B back to its original position when solenoid 30 becomes deactuated. Although a matter of design choice, applicant contemplates that nose 34 may be extended up to 1.50 inches in order to depress a desired key of computer keyboard C. Solenoid 30 is most suitably a Size 75 Push Solenoid Stock Model 178764-029 available from Lucas Ledex, Inc. of Vandalie, Ohio.

Whereas pointer 20 may be pivoted inwardly and vertically upwardly/downwardly about horizontal axis X and horizontal axis Y of support arm 14, horizontal pivotal movement which is necessary to access the entirety of computer keyboard C is achieved by virtue of the articulating construction of proximal section 24 and distal section 26 of pointer 20 which will be described in detail hereinafter.

Figure 4:
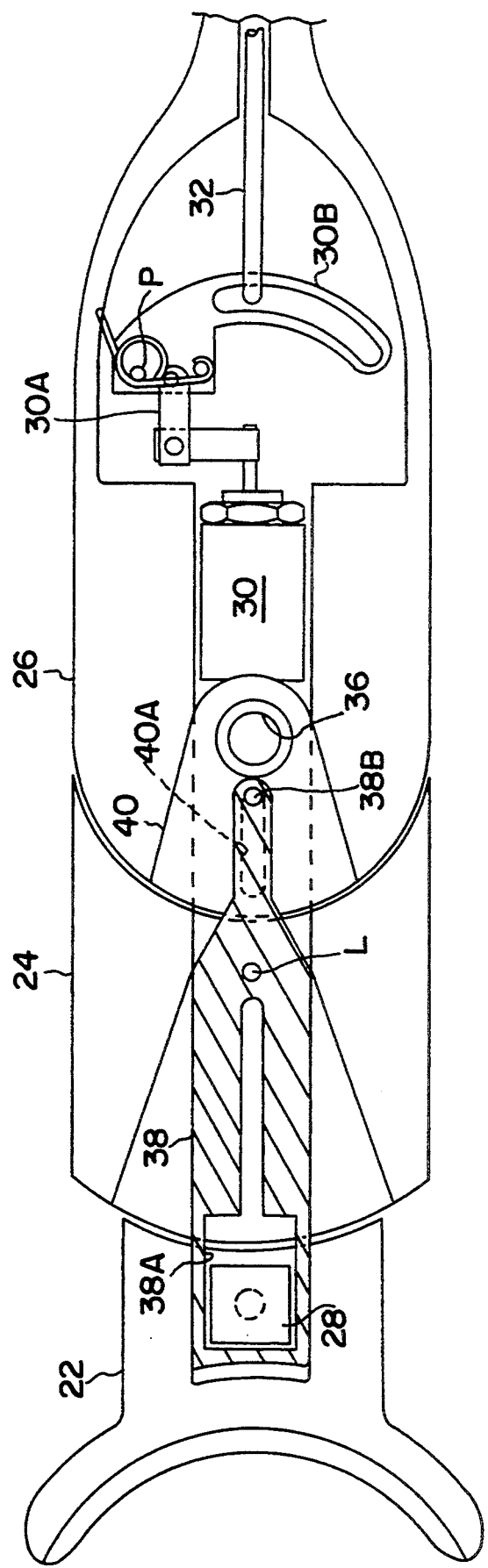
FIG. 4 is a horizontal sectional view of the pointer element of the device of the present invention wherein the pointer element has not been articulated.

Referring now specifically to drawings 4–6, the lateral pivoting movement of pointer 20 can be better understood. In FIG. 4 pointer 20 is in its non-articulated position with proximal section 24 and distal section 26 being positioned lengthwise relative to each other. In FIG. 5, pointer 20 has been articulated horizontally to the left (with the pointer facing the computer keyboard C) by pivotably moving proximal section 24 relative to distal section 26. In FIG. 6, nose 34 of articulated pointer 20 has been actuated and caused to extend outwardly in order to depress a selected computer keyboard key (not shown). The specifics of the pivoting horizontal movement of pointer 20 will now be explained in detail with reference again to FIGS. 4–6 as well as the exploded view of pointer 20 shown in FIG. 7.

As noted previously, the upper and lower housing sections of chin engagement 22, proximal section 24 and distal section 26 are secured together in order to construct pointer 20 and to contain the electromechanical components thereof within the interior thereof. A pivot collar 36 extends between the front portion of the upper housing of proximal section 24 and the back portion of the lower housing of distal section 26 (see FIG. 7) and provides for pivotal movement of proximal section 24 relative to distal section 26 (see FIGS. 4–6). Cam actuator lever 38 is secured at its proximal end between the upper and lower housings of chin engagement 22 and defines an aperture 38A therein for snugly receiving transducer 28. Cam actuator lever 38 is secured within proximal section 24 so as to pivot about pivot axis L. The distal end of cam actuator lever 38 includes a detente 38B which cooperates with pivot cam 40 secured to the rear portion of distal section 26 so that horizontal movement of chin engagement 22 by the operator of pointer 20 serves to urge detente 38B of cam actuator lever 38 against the slot 40A of pivot cam 40 so as to pivotably rotate distal section 26 relative to proximal section 24 (see FIGS. 5-6). Cam actuator lever 38 and pivot cam 40 are most suitably formed so that horizontal movement of chin engagement 22 is multiplied in its translation to horizontal movement of distal section 26 and nose 34.

The uniqueness of the articulation of pointer 20 can be particularly appreciated with reference to FIGS. 5 and 6 where it can be seen that movement of chin engagement 22 to the left by the operator of pointer 20 results in movement to the left by distal section 26 and nose 34 carried thereby. In this fashion, an operator of device 10 is able to properly position nose 34 adjacent a key to be depressed on computer keyboard C by inward and vertical pivotal movement of pointer 20 about axes X and Y of support arm 14 and/or by left or right horizontal pivotal movement of nose 34 by left or right movement of chin engagement 22.

Figure 2:
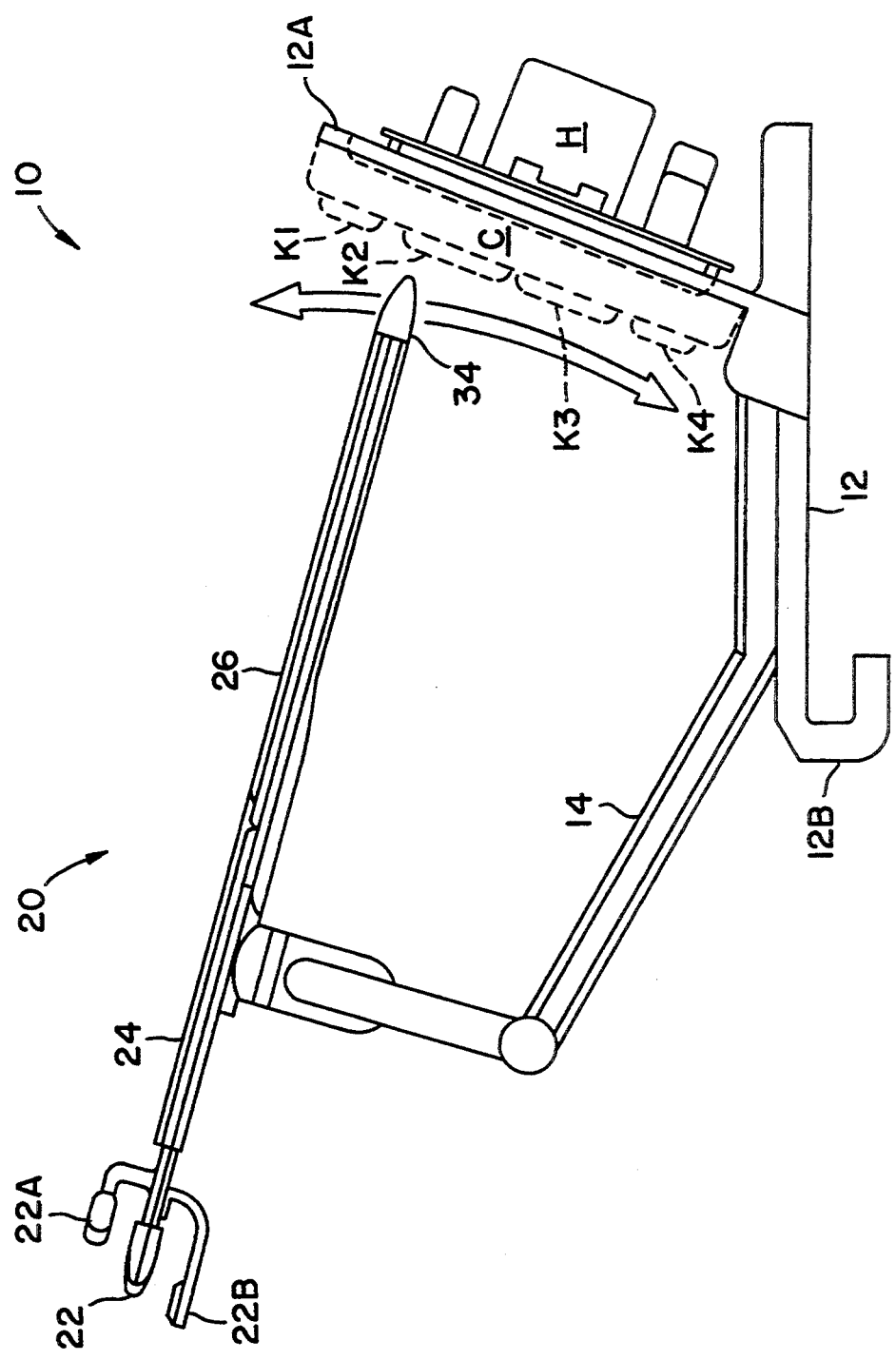
FIG. 2 is a side elevation view of the device of the present invention.
Figure 3:
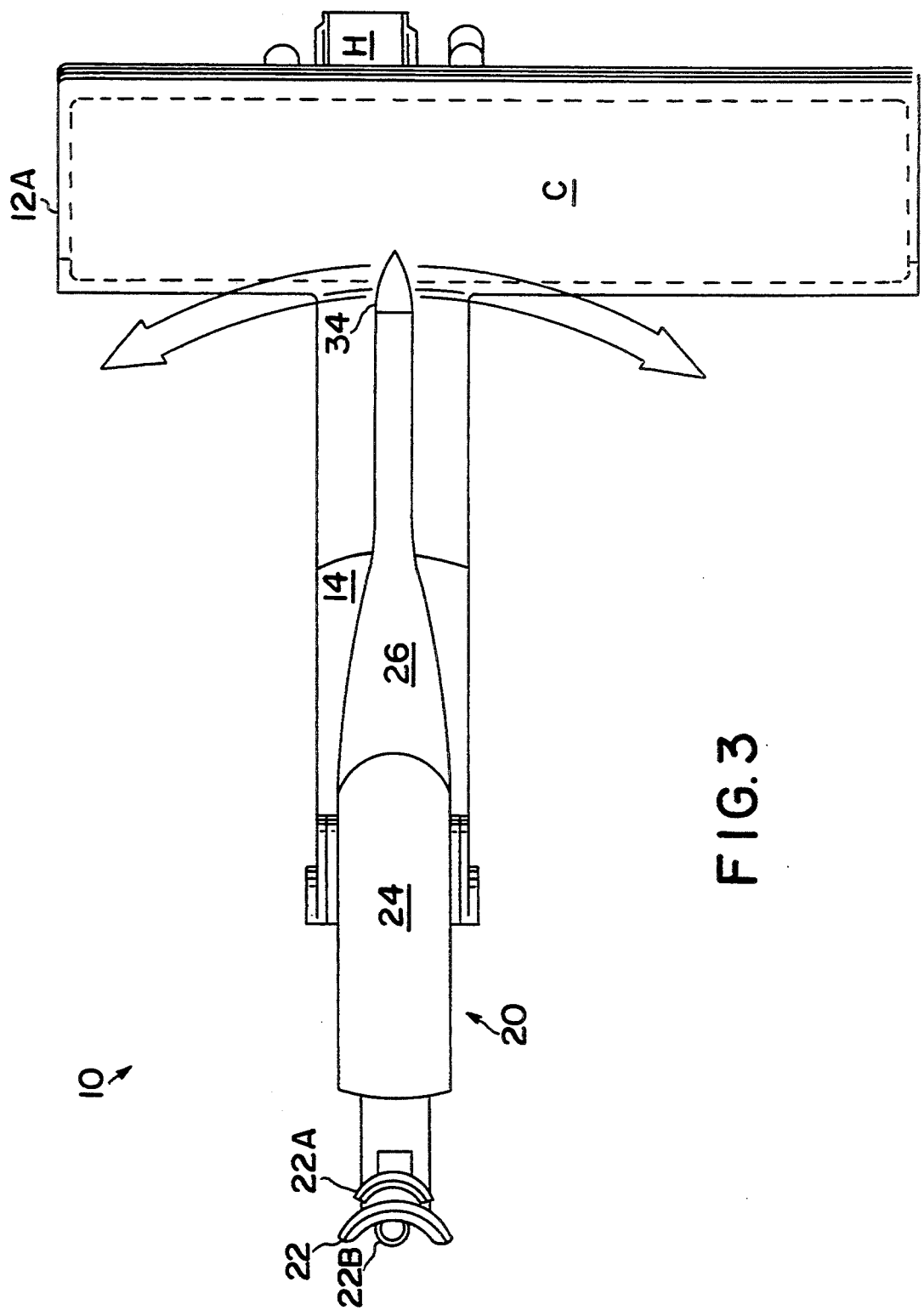
FIG. 3 is a top plan view of the device of the present invention.

Once nose 34 of pointer 20 has been properly vertically and horizontally positioned adjacent a computer keyboard key to be depressed, the operator of device 10 exhausts a breath into breath port 22A which is detected by pressure sensor transducer 28. Transducer 28 creates a low level electrical signal which is carried by suitable electrical wiring (not shown) to electrical circuitry contained within a housing H secured to the back of the inclined support 12A of base 12 (see FIGS. 1 and 2). The circuitry contained within housing H serves to convert the low level electrical signal from transducer 28 to a high current pulse which is then carried by suitable wiring (not shown) to solenoid 30 for actuation thereof.

With reference specifically to FIG. 6, it can be seen that solenoid 30 when actuated by the high current pulse created by the circuitry within housing H (a representative circuit being shown in FIG. 8E) pushes solenoid cam link 30A outwardly and thereby serves to pivot nose extender cam 30B about pivot axis P to force link rod 32 and nose 34 secured to the end thereof momentarily outwardly. Solenoid 30 when deactuated and spring 30C will serve to withdraw nose 34 from its extended position back to its retracted position within the forward end of distal section 26 of pointer 20. Applicant wishes to note that although a push-type solenoid and cam arrangement is shown in the drawings and described herein, it is also clearly within the scope of applicant's invention to incorporate a pull-type solenoid and a suitable operatively connected cam in order to extend link rod 32 and nose 34 to depress a selected key on a computer keyboard which is being addressed by the device 10 of the present invention.

In use, device 10 is a chin-controlled actuator for making personal computers accessible to handicapped individuals having little or no use of their hands. Applicant specifically contemplates that spinal cord injured people who have full use of their head and neck would be the primary group to find utility in the present invention. Device 10 would be positioned directly in front of a personal computer monitor (not shown) so that the leading edge 12B of base 12 would extend over the front edge of the work surface. To operate device 10, the operator would first wheel up to his work station, position himself in front of the computer with computer keyboard C properly positioned on inclined support 12A of base 12 of the device of the invention. The operator then would rest his chin on chin rest 22B. To select and input data into computer keyboard C, after inward and vertical adjustment of pointer 20, the operator would simply pivot his head against chin engagement 22 and nose 34 will follow in the direction of horizontal pivot. When nose 34 is in position over a key to be depressed, the operator merely exhausts a light puff of breath into breath port 22A to cause nose 34 to be outwardly motivated and depress the selected key.

Applicant contemplates that the operator will merely rest his chin on chin rest 22B and will maintain his mouth spaced apart from breath port 22A so that no part of device 10 is placed into his mouth and thus device 10 is maintained in a hygienically clean state. Minimum fatigue is incurred by the operator of device 10 and work performance is enhanced over prior art "head sticks" and "mouth sticks" which have been discussed in some detail above.

Electrical Circuitry

Applicant will now provide a detailed description of a representative circuit which can be used with the instant invention in order to provide motivation to nose 34 by means of an air puff into breath port 22A. However, applicant wishes to again observe that other suitable circuits can be designed to enhance the signal from air sensor transducer 28 to solenoid 30, and that the circuitry shown in FIGS. 8A-8E is merely an illustration of a representative circuit which could be used in applicant's novel device and is not intended to limit the invention.

The circuit can be broken into four sections. They are (1) the power supply, (2) voltage amplification, (3) pulse forming and (4) driver sections.

Power Supply

Figure 8A:
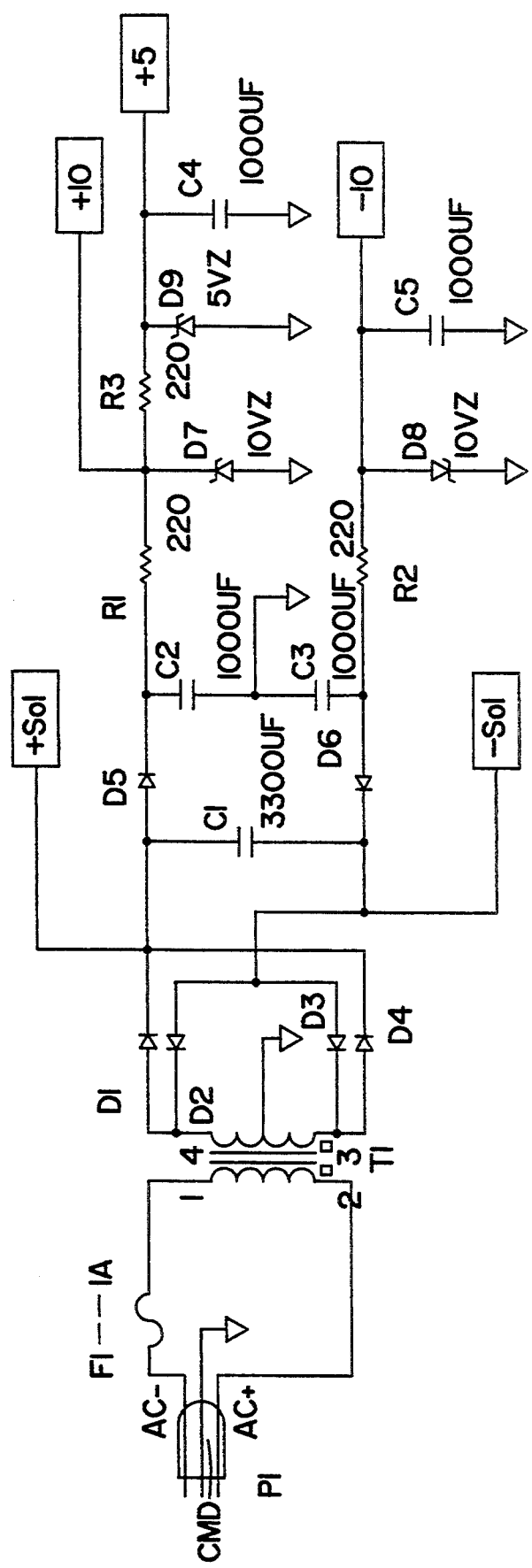
FIGS. 8A–8E are schematic diagrams of one possible electric circuit for the device of the present invention.

The purpose of the power supply section (see FIG. 8A) is to provide DC bias voltage and operating current used to sustain operation of the amplification, pulse forming, and current driver sections. FIG. 8A depicts the power supply section. The circuit is intended to be operated at 120 VAC and 60 HZ. A 120 VAC source (United States wall outlet voltage) is connected to the circuit by P1. P1 has connections for the conventional hot, neutral, and ground (green wire). Wiring at the input to the transformer is protected by fuse F1. The purpose of F1 is to disconnect the circuit from the line in the event of a sustained over current.

The line voltage is stepped down by transformer T1 from 120 VAC nominal to 32 VAC with a split centered tap. Diodes D1, D2, D3 and D4 make up a dual full wave rectifier supplying both + and − full wave rectified voltage. Diodes D1 and D4 provide + rectified voltage, and diodes D2 and D3 provide full wave rectified voltage. Capacitor C1 spans the + and − supply acting as a smoothing device as well as a storage device. The purpose of diode D5 is to allow positive current to pass to capacitor C2 and prevent positive current from being delivered from C2 to C1. Capacitor C2 acts as a filter removing AC voltage component.

The combination of resistor R1 and Zener diode D7 provide a +10 volt bias supply. Resistor R1 limits current into Zener D7 and the load. Zener diode D7 clamps the voltage presented to its cathode to 10 volts. This provides a regulated voltage which is used to operate linear electronics (IC 1). The combination of resistor R3 and Zener diode D9 provide a +10 volt bias supply. Resistor R3 limits current into Zener diode D9 and the load. Zener diode D9 clamps the voltage presented to its cathode to 5 volts. This provides a regulated voltage which is used to operate digital electronics (IC2). The combination of resistor R2 and Zener diode D8 provide a −10 volt bias supply. Resistor R2 limits current into Zener diode D8 and the load. Zener diode D8 clamps the voltage presented to its anode to −10 volts. This provides a regulated voltage which is used to operate linear electronics (IC1). The purpose of diode D6 is to allow negative current to pass to capacitor C3 and prevent negative current from being delivered from C3 to C1. Capacitor C3 acts as a filter removing AC voltage components.

Voltage Amplification

The purpose of the voltage amplification section (see FIG. 8B) is to increase the electrical signal produced by the pressure sensor 28 to a magnitude which can be used to trigger a pulse circuit. Pressure sensor 28 is a barometric pressure transducer which converts the effect of pressure presented to its input port to a differential voltage signal. The magnitude of the signal is proportional to the magnitude of pressure presented to the pressure input port.

Figure 8B:
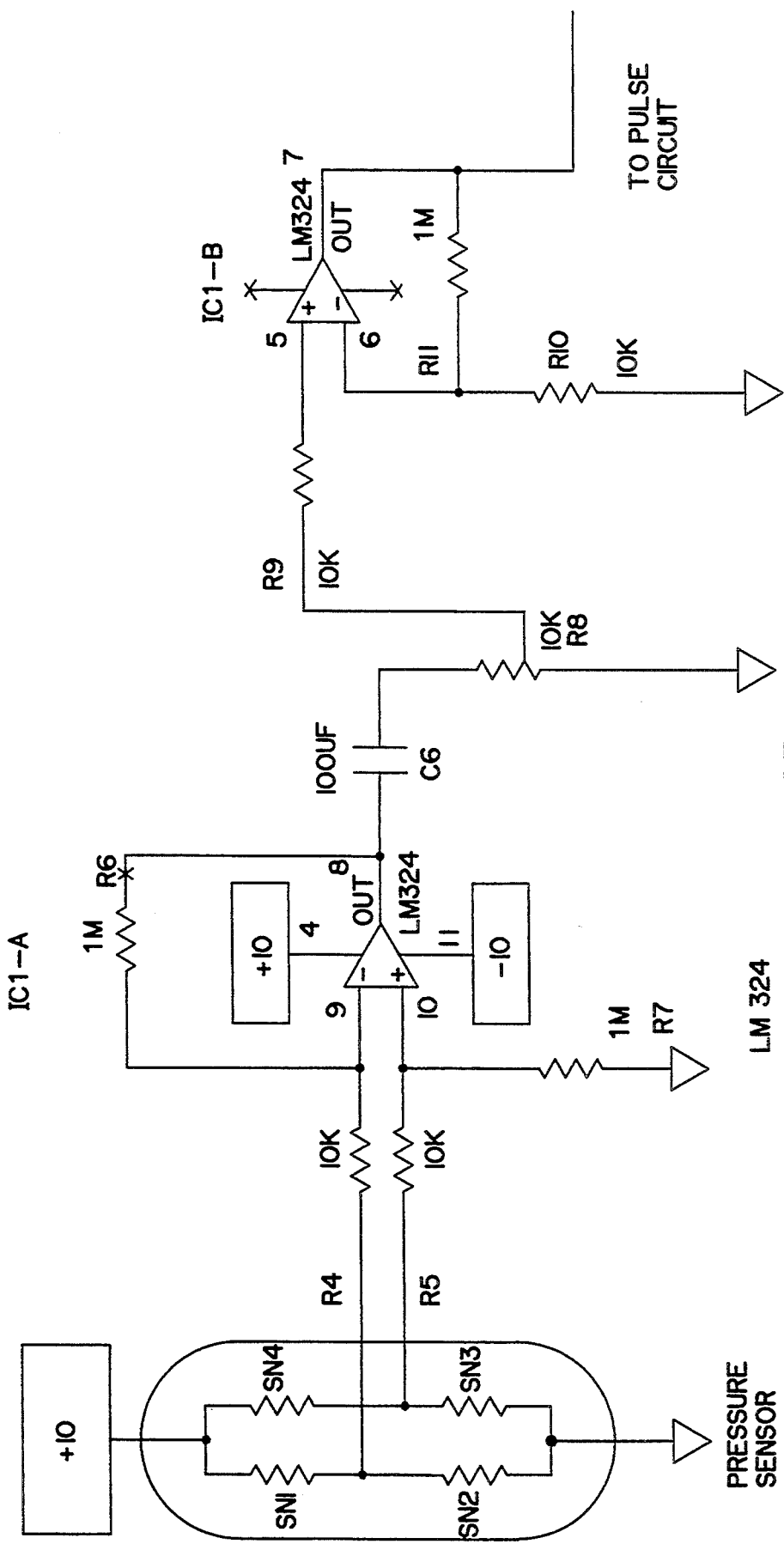

FIG. 8B depicts sensor S1 and the voltage amplification section. As pressure is increased at the pressure sensor input port, a differential resistance is created within the sensor. The sensor resistor configuration is a resistive bridge. A bias voltage (10 volts) is applied to the top of the bridge. Changes in pressure are converted to changes in bridge resistance which then produce a differential voltage proportion to the pressure difference. Resistors R4, R5, R6 and R7 together with IC1 section A make up a differential voltage amplifier. A differential amplifier is used to exploit the bridge-type sensor and to increase noise immunity. The gain of the amplifier shown in FIG. 8B is approximately 10,000. Capacitor C6 AC couples the signal to potentiometer P1. The purpose of potentiometer R8 is to allow the sensitivity of the system to be controlled.

The second amplifier is a single ended voltage amplifier having a maximum gain of 100. Resistors R9, R10, R11 and IC1-B make up the amplifier. The output of IC1-B is DC coupled to the input of the digital pulse forming section.

In this description of amplifiers applicant has stated the gains of the amplifiers. The value of the amplifier gains are for reference only. Gains were selected to allow operation with a particular sensor. Use of other sensors of similar electrical characteristics but different transducer efficiency will require modification of the gains.

Pulse Forming Section

Figure 8C:
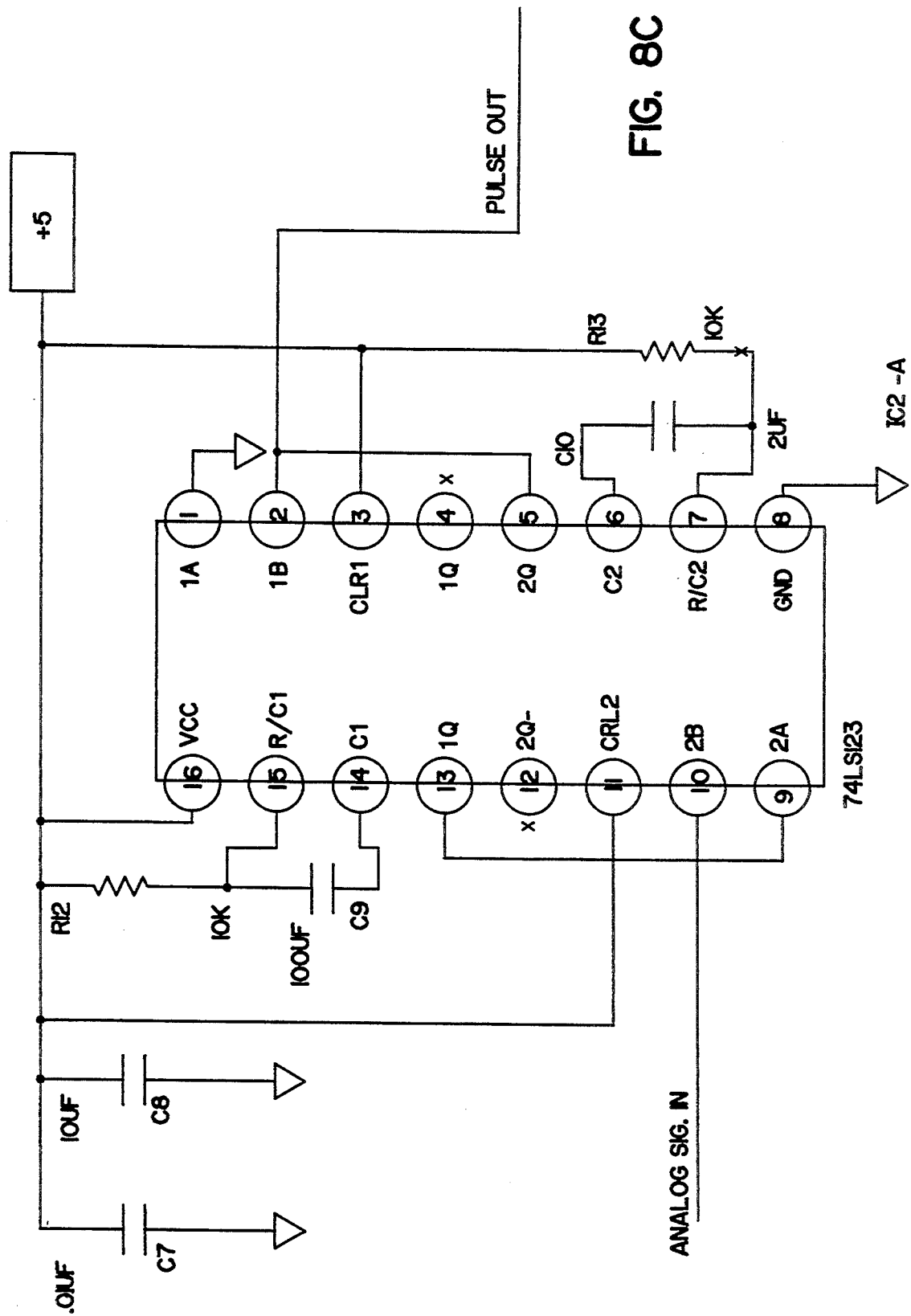
Figure 8E:
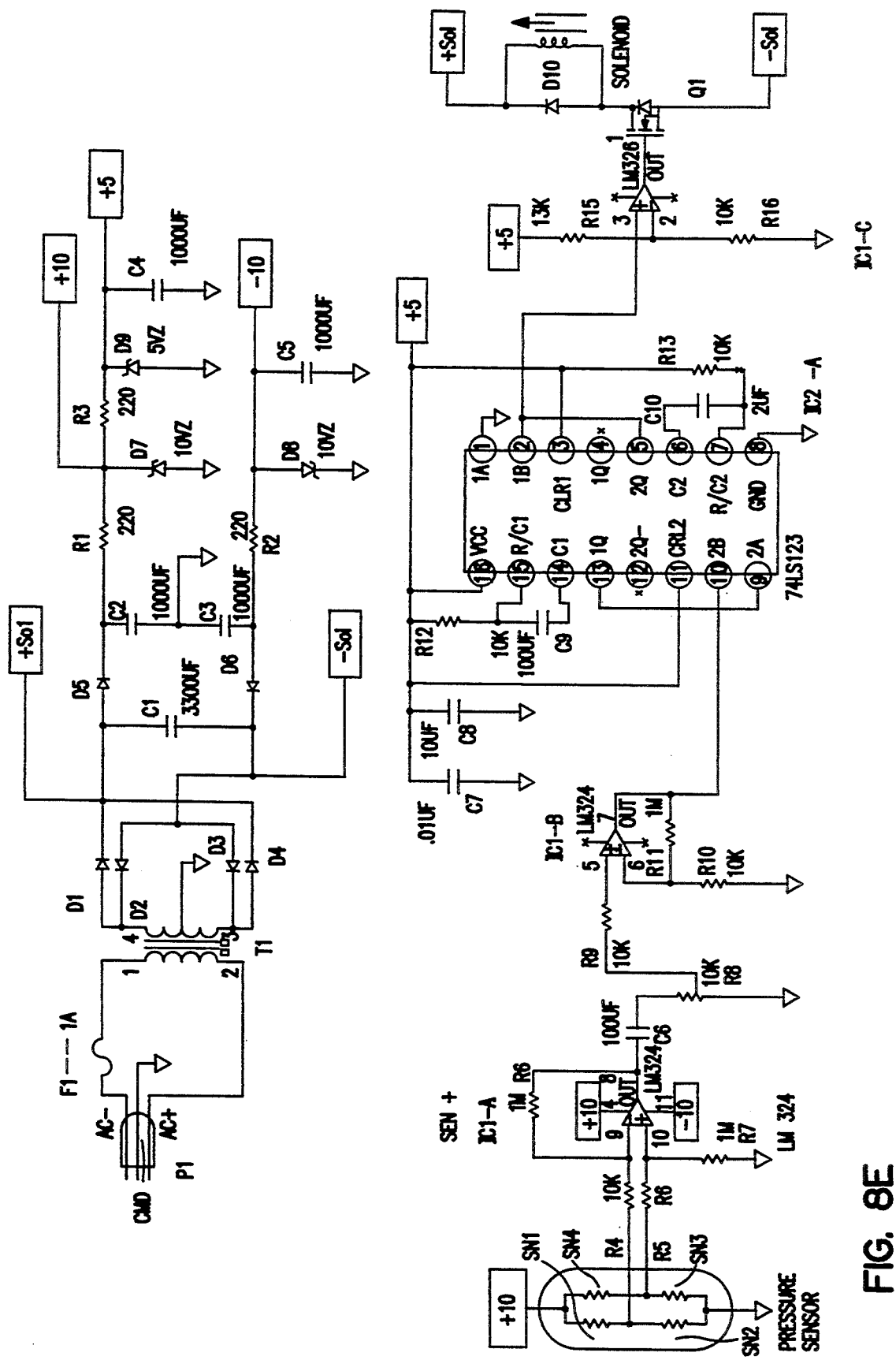

The purpose of the pulse forming section (see FIG. 8C) is to produce a pulse of specific amplitude and timing. The pulse is later used to drive solenoid 30 which is the prime mover to the mechanical portion of the invention. FIG. 8C depicts the pulse forming section. The pulse forming section is divided into two sections. A pulse producing section and a pulse lockout section. The pulse forming section consists of capacitors C10 and R13 which program section 2 of IC2 (74LS123). The values of C10 and R13 allow a pulse of a specific up time (approximately 150 ms) to be produced when the gate is triggered. For a pulse to be emitted IC2 input 2A must be driven low and 2B must be drive high. Input 2A is connected to the output of the second section of the IC2 (1Q). Input 2B is connected to the output of the second voltage amplifier IC1 pin 7. When voltage at input 2B exceeds the trigger voltage (about 1.5 volts) a pulse is produced at output 2Q.

When output 2Q switches high section 1 of the IC is triggered producing a pulse. The duration of the pulse is determined by C9 and R12 and is approximately 500 ms. The pulse is present at 1Q which has switched high. 1Q is connected to input 2A. In this state section 2 cannot be re-triggered until the pulse at 1Q is completed and switches low. This prevents 2Q from being triggered until 1Q has timed out. The dual timer function is necessary to eliminate continuous triggering caused by excessively long pressure changes at transducer 28 (e.g., the user blows into the sensor producing more output pulses than needed). Capacitors C7 and C8 are used to eliminate and decouple power supply noise from entering and leaving the IC.

Solenoid Driver Section

Figure 8D:
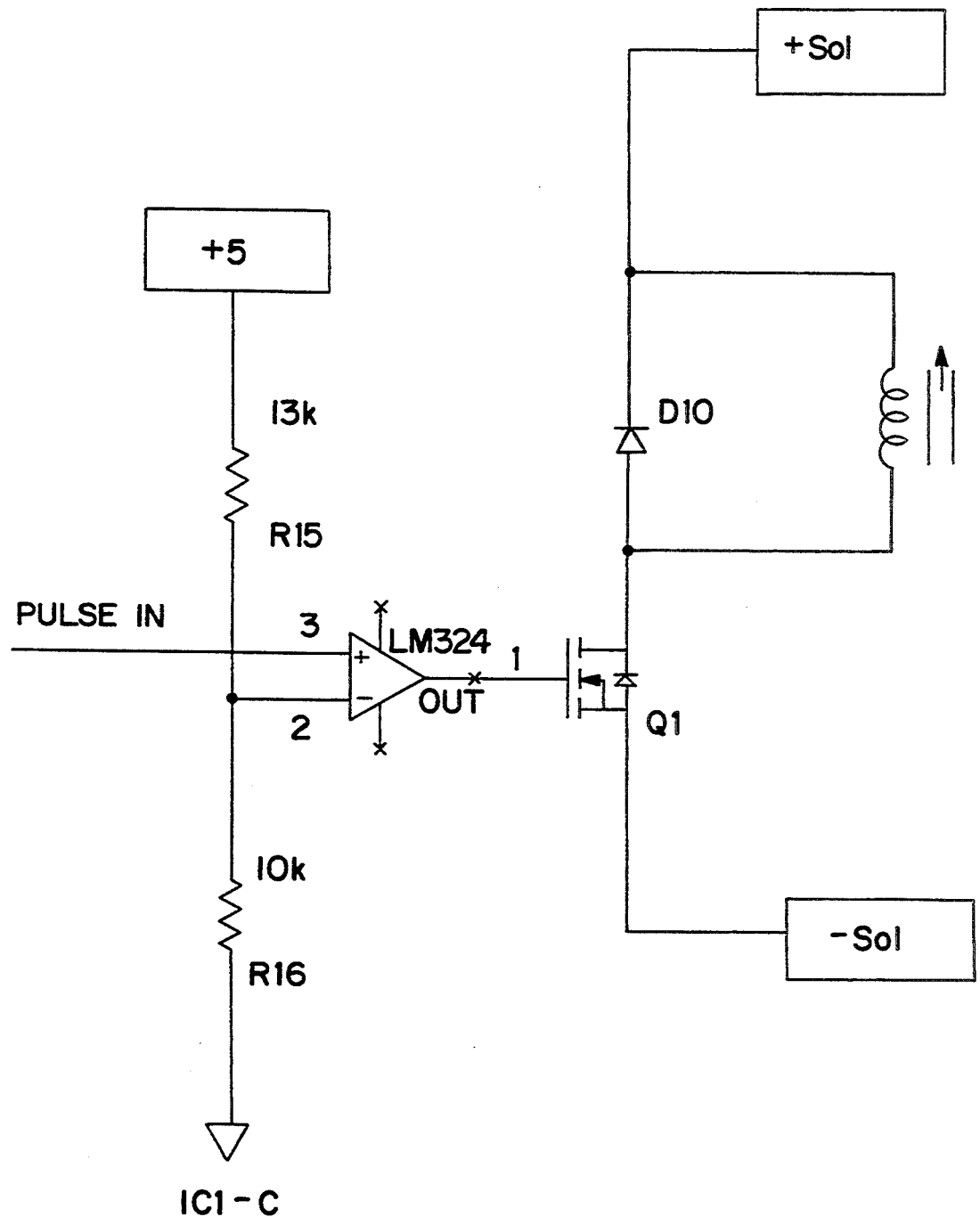

The purpose of the solenoid driver section (see FIG. 8D) is to amplify the pulse formed by previous stages to a magnitude capable of driving a solenoid load. FIG. 8D depicts the solenoid driver section. The solenoid driver consists of resistors R15 and R16, IC1 section C, diode D10 and power Field Effect Transistor (FET) Q1. Resistors R15 and R16 form a voltage divider establishing a switching threshold (2.2 volts) for the output switch driver IC1-C. IC1-C provides the voltage drive to operate the Gate of Q1. Q1 acts as a high current switch allowing current to pass through the solenoid. Diode D10 is connected across the solenoid. Its purpose is to dissipate the negative voltage transient produced by the collapsing magnetic field within the solenoid at turn off.

Overall Schematic Diagram

The overall schematic diagram incorporating all of the sections described above is shown in FIG. 8E.

Alternative Embodiments of the Invention

Applicant has described hereinabove a preferred embodiment of the device of the instant invention which is adapted to mount to a work surface and which provides a base support including support means for a computer keyboard or the like. However, applicant contemplates other embodiments of the "power pointer" invention which would be adapted for mounting to the body of the operator and which would not require or include a base as described hereinabove. These alternative embodiments of the invention would incorporate all of the electrical circuitry within the body of the pointer element and would comprise the pointer element and a suitable support means for securing same to the body of the operator.

Thus, it will be understood that various details of the invention may be changed without departing from the scope of the invention. Furthermore, the foregoing description is for the purpose of illustration only, and not for the purpose of limitation—the invention being defined by the claims.

What is claimed is:

1. A device for permitting a person with limited or no use of the hands to operate the keyboard of a computer, said device comprising:
   a base including means for supporting a computer keyboard in a generally upright position for easy viewing of the keyboard by an operator of said device;

support arm means extending from said base and secured at one end thereto, said support arm means comprising an articulated arm for pivotal vertical movement of said elongate pointer element; and an elongate pointer element adjustably mounted at the other end of said support arm means for operative engagement of selected keys of a computer keyboard positioned on said base and having a proximal end engageable by the face of the operator and a distal end selectively actuateable to move from a first retracted position to a second extended position and back to said retracted position, said elongate pointer element comprising operator face actuator means for allowing the operator to position the distal end of said elongate pointer element adjacent a desired key of said computer keyboard and to then actuate said distal end so as to depress said selected keys.

2. A device according to claim 1 wherein said means for supporting a computer keyboard comprises a generally upright planar support surface.

3. A device according to claim 1 wherein said operator actuator means of said elongate pointer element comprises:
   a breath actuated transducer positioned in the proximal end of said elongate pointer element;
   a solenoid operatively connected to said distal end of said pointer element; and
   circuit means electrically connecting said transducer and said solenoid;
   whereby actuation of said transducer by the operator serves to actuate said solenoid and said distal end.

4. A device according to claim 1 wherein said elongate pointer element comprises first and second horizontally articulated sections wherein the first section includes said proximal end of said pointer element and the second section includes said movable distal end of said pointer element, said articulated sections being adapted for movement so that pivotal movement of said proximal end of said elongate pointer element causes pivotal movement of said distal end of said pointer element in the same direction as the pivotal movement of said proximal end by means of a lever and pivot cam mechanism connecting said first and second sections.

5. A device according to claim 4 wherein said proximal end of said pointer element includes a chin rest and a face engagement element.

6. A device for permitting a person with limited or no use of the hands to operate the keyboard of a computer, said device comprising:
   a base including means for supporting a computer keyboard in a generally upright position for easy viewing of the keyboard by an operator of said device;
   support arm means extending from said base and secured at one end thereto; and
   an elongate pointer element adjustably mounted at the other end of said support arm means for operative engagement of a computer keyboard positioned on said base and having a proximal end engageable by the face of the operator and a distal end selectively actuateable to move from a first retracted position to a second extended position and back to said retracted position, said elongate pointer element comprising an operator face actuated transducer positioned in the proximal end of said pointer element, a solenoid operatively connected to said movable distal end of said elongate pointer element, and circuit means electrically connecting said operator actuated transducer and said solenoid;
   whereby actuation of said transducer by the operator serves to actuate said solenoid and said distal end.

7. A device according to claim 6 wherein said means for supporting a computer keyboard comprises a generally upright planar support surface.

8. A device according to claim 6 wherein said support arm means comprises an articulated arm for pivotal vertical movement of said elongate pointer element.

9. A device according to claim 6 wherein said transducer is a breath actuated transducer.

10. A device according to claim 6 wherein said elongate pointer element comprises first and second horizontally articulated sections wherein the first section includes said proximal end of said pointer element and the second section includes said movable distal end of said pointer element, said articulated sections being adapted for movement so that pivotal movement of said proximal end of said elongate pointer element causes pivotal movement of said distal end of said pointer element in the same direction as the pivotable movement of said proximal end by means of a lever and pivot cam mechanism connecting said first and second sections.

11. A device according to claim 10 wherein said proximal end of said pointer element includes a chin rest and a face engagement element.

12. A device for permitting a person with limited or no use of the hands to operate the keyboard of a computer, said device comprising:
   a base including means for supporting a computer keyboard in a generally upright position for easy viewing of the keyboard by an operator of said device;
   pivotable adjustable support arm means extending from said base and secured at one end thereto; and
   an elongate pointer element adjustably mounted at the other end of said support arm means for operative engagement of a computer keyboard positioned on said base and having a proximal end engageable by the face of the operator and a distal end selectively actuateable to move from a first retracted position to a second extended position and back to said retracted position, said elongate pointer element comprising an operator breath actuated transducer positioned in the proximal end of said pointer element, a solenoid operatively connected to said distal end of said pointer element for moving said distal end from said first retracted position to said second extended position and back to said retracted position, and circuit means electrically connecting said transducer and said solenoid;
   whereby intermittent breath actuation of said transducer by the operator serves to actuate said solenoid and said distal end.

13. A device according to claim 12 wherein said means for supporting a computer keyboard comprises a generally upright planar support surface.

14. A device according to claim 12 wherein said elongate pointer element comprises first and second horizontally articulated sections wherein the first section includes said proximal end of said pointer element and the second section includes said movable distal end of said pointer element, said articulated sections being adapted for movement so that pivotal movement of said proximal end of said elongate pointer element causes pivotal movement of said distal end of said pointer element in the same direction as the pivotal movement of the proximal end by means of a lever and pivot cam mechanism connecting said first and second sections.

15. A device according to claim 12 wherein said proximal end of said pointer element includes a chin rest and a face engagement element.

16. A device according to claim 15 wherein said proximal end of said pointer element further includes a port member having an air passageway to said transducer for receiving said intermittent breaths of air from the operator during use of said device.

17. A device for permitting a person with limited or no use of the hands to operate the keyboard of a computer, said device comprising:

support means adapted for securement at one end to the body of an operator or to a work surface; and an elongate pointer element adjustably mounted at the other end of said support means for operative engagement of a computer keyboard and having a proximal end engageable by the face of the operator and a distal end selectively actuateable to move from a first retracted position to a second extended position and back to said retracted position, said elongate pointer element comprising operator face actuator means for allowing the operator to position the distal end of said elongate pointer element adjacent a desired key of said computer keyboard and to then actuate said distal end so as to depress said computer keyboard key;

wherein said operator face actuator means comprises a breath actuated transducer positioned in the proximal end of said elongate pointer element, a solenoid operatively connected to said distal end of said pointer element, and circuit means electrically connecting said transducer and said solenoid;

whereby actuation of said transducer by the operator serves to actuate said solenoid and said distal end to actuate selected keyboard keys.

18. A device according to claim 17 wherein said elongate pointer element comprises first and second horizontally articulated sections wherein the first section includes said proximal end of said pointer element and the second section includes said movable distal end of said pointer element, said articulated sections being adapted for movement so that pivotal movement of said proximal end of said elongate pointer element causes pivotal movement of said distal end of said pointer element in the same direction as the pivotal movement of said proximal end by means of a lever and cam mechanism connecting said first and second sections.

* * * * *